(12) United States Patent
Ravetch

(10) Patent No.: US 6,676,927 B1
(45) Date of Patent: Jan. 13, 2004

(54) ANIMAL MODEL AND METHODS FOR ITS USE IN THE SELECTION OF CYTOTOXIC ANTIBODIES

(75) Inventor: Jeffrey V. Ravetch, New York, NY (US)

(73) Assignee: The Rockefeller University, New York, NY (US)

( * ) Notice: Subject to any disclaimer, the term of this patent is extended or adjusted under 35 U.S.C. 154(b) by 0 days.

(21) Appl. No.: 09/481,175

(22) Filed: Jan. 12, 2000

Related U.S. Application Data
(60) Provisional application No. 60/116,972, filed on Jan. 20, 1999.

(51) Int. Cl.$^7$ .............................................. G01N 33/00
(52) U.S. Cl. .................. 424/9.2; 530/387.1; 530/387.3; 424/130.1
(58) Field of Search .......................... 800/3, 8, 11, 18; 530/388.8, 388.85, 387.1, 387.3; 424/130.1, 133.1, 9.2

(56) References Cited

U.S. PATENT DOCUMENTS 5,530,179 A * 6/1996 Terhorst et al.
5,877,396 A * 3/1999 Ravetch et al.

FOREIGN PATENT DOCUMENTS

WO  WO 99/51642  10/1999

OTHER PUBLICATIONS

Allison et al., 1996, "Antibody dependent cell–mediated cytotoxicity (ADCC) of an anti–HER2 antibody requires opsonization of tumor target", FASEB Abstract/Poster.
Bolland et al., 1998, "SHIP modulates immune receptor responses by regulating membrane association of Btk", Immunity 8:509–516.
Carter et al., 1992, "Humanization of an anti–p185$^{HER2}$ antibody for human cancer therapy", Proc. Natl. Acad. Sci. USA 89:4285–4289.
Clynes et al., 1998, "Uncoupling of immune complex formation and kidney damage in autoimmune glomerulonephritis", Science 279:1052–1054.
Clynes et al., 1998, "Fc receptors are required in passive and active immunity to melanoma", Proc. Natl. Acad. Sci. USA 95:652–656.
Clynes ey al., 1999, "Modulation of immune complex–induced inflammation in vivo by the coordinate expression of activation and inhibitory Fc receptors", J. Exp. Med. 189:179–185.
Clynes and Ravetch, 1995, "Cytotoxic antibodies trigger inflammation through Fc receptors", Immunity 3:21–26.
Diamond and Yelton, 1981, "A new Fc receptor on mouse macrophages binding IgG$_3$ ", J. Exp. Med. 153:514–519.
Hara et al., 1995, "Implicating a role for immune recognition of self in tumor rejection: passive immunization against the Brown locus protein", J. Exp. Med. 182:1609–1614.

Hazenbos, 1996, Impaired IgG–dependent anaphylaxis and Arthus reaction in FcγRIII(CD16) deficient mice, Immunity 5:181–188.
Heiken et al., 1996, "T lymphocyte development in the absence of Fcε receptor Iγ subunit: analysis of thymic–dependent and independent αβ and γδ pathways", Eur. J. Immunol. 26:1935–1943.
Hotaling et al., 1996, "The humanized anti–HER2 antibody rhuMAb HER2 mediates antibody dependent cell–mediated cytotoxicity via FcγR III", AACR Abstract/Poster.
Houghton, 1994, "Cancer antigens: immune recognition of self and altered self", J. Exp. Med. 180:1–4.
Jaffe and Perdoll, 1996, "Murine tumor antigens: is it worth the search?", Curr. Opin. Immunol. 8:622–627.
Li et al., 1996, "Reconstitution of human FcγRIII cell type specificity in transgenic mice", J. Exp. Med. 183:1259–1263.
Naftzger et al., 1996, "Immune response to a differentiation antigen induced by altered antigen: a study of tumor rejection and autoimmunity", Proc. Natl. Acad. Sci. USA 93:14809–14814.
Okada et al., 1998, "Cutting edge: role of the inositol phosphatase SHIP in B cell receptor–induced Ca$^{2+}$ oscillatory response", J. Immunol. 161:5129–5132.
Ono et al., 1996, "Role of the inositol phosphatase SHIP in negative regulation of the immune system by the receptor FcγRIIB", Nature 383:263–266.
Ono et al., 1997, "Deletion of SHIP or SHP–1 reveals two distinct pathways for inhibitory signaling", Cell 90:293–301.
Presta et al., 1994, "The binding site on human immunoglobulin E for its high affinity receptor", J. Biol. Chem. 269:26368–26373.
Ravetch and Clynes, 1998, "Divergent roles for Fc receptors and complement in vivo",Ann. Rev. Immunol. 16:421–432.
Ravetch, 1994, "Fc receptors: Rubor redux", Cell 78:553–560.
Ravetch, 1997, "Fc receptors", Curr. Opin. Immunol. 9:121–125.
Shores et al., 1998, "T cell development in mice lacking all T cell receptor ζ family members (ζ, η, and FcεRIγ)", J. Exp. Med. 187:1093–1101.

(List continued on next page.)

Primary Examiner—Larry R. Helms
(74) Attorney, Agent, or Firm—Pennie & Edmonds LLP

(57) ABSTRACT

The present invention relates to non-human animals and in vivo methods for testing the efficacy of antibodies directed to antigens expressed by tumors in such animals. In particular, the invention relates to an animal deficient in the expression of one or more Fc receptors. Additionally, such an animal is also immunodeficient, and thus permits the growth of a xenogeneic tumor implant. Such immunodeficient animals may also express human receptors. The present invention also relates to methods of evaluating the enhanced ability of an existing antibody or Fc-modified antibody to act as an immunotherapeutic to eradicate tumor cells or infectious agents.

16 Claims, 14 Drawing Sheets

OTHER PUBLICATIONS

Figure 1A:
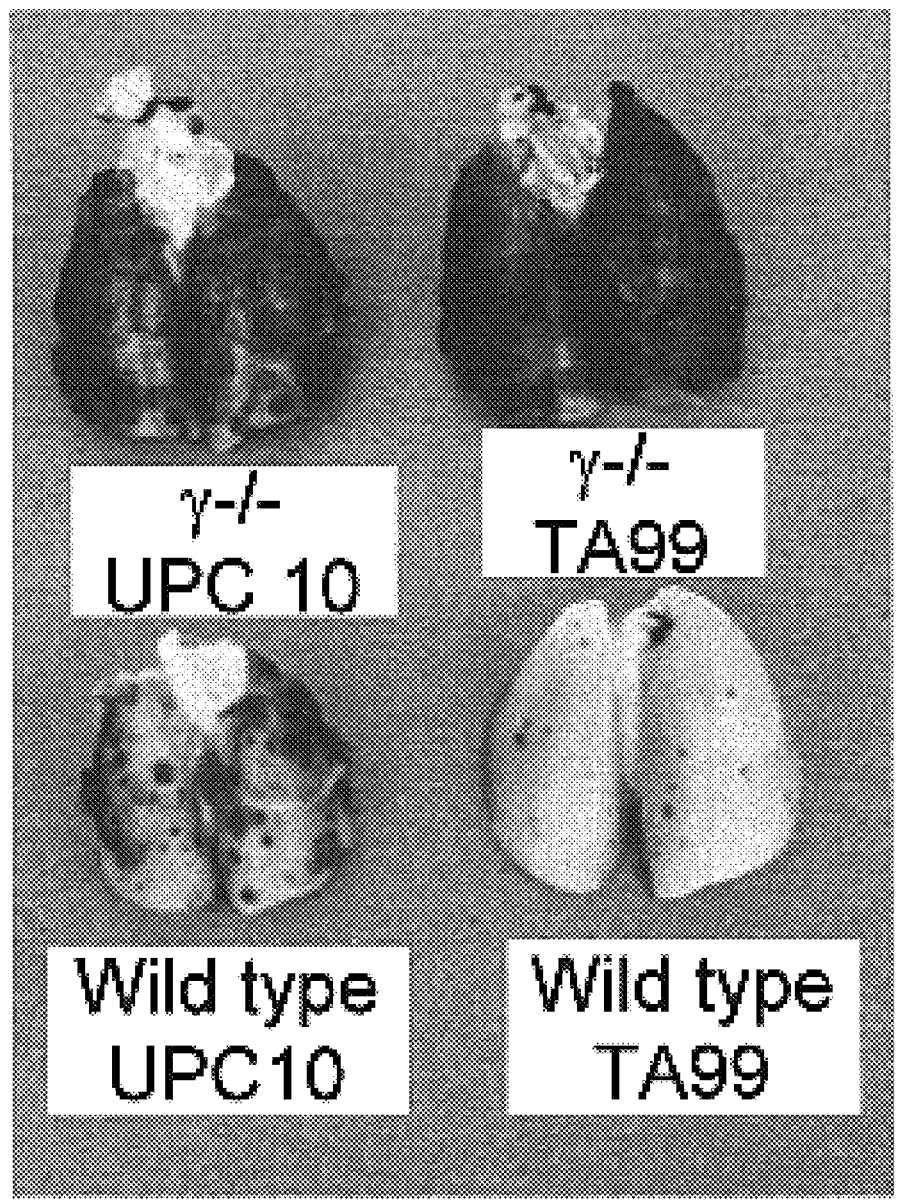

Suzuki et al., 1998, "Distinct contribution of Fc receptors and angiotensin II–dependent pathways in anti GBM glomerulonephritis", Kidney Int. 54:1166–1174.

Sylvestre et al., 1996, "Immunoglobulin G–mediated inflammatory responses develop normally in complement–deficient mice", J. Exp. Med. 184:2385–2392.

Sylvestre and Ravetch, 1996, "A dominant role for Mast cell Fc receptors in the Arthus reaction", Immunity 5:387–309.

Sylvestre and Ravetch, 1994, "Rc receptors initiate the Arthus reaction: redefining the inflammatory cascade", Science 265:1095–1098.

Takai et al., 1994, "FcR γ chain deletion results in Pleiotrophic effector cell defects", Cell 76:519–529.

Takai et al., 1996, "Augmented humoral and anaphylactic responses in FcγRII–deficient mice", Nature 379:346–349.

Takechi et al., 1996, "A melamosmal membrane protein is a cell surface target for melanoma therapy", Clin. Cancer Res. 2:1837–1842.

Yuan et al., 1998, "Antibody–mediated modulation of *Cryptococcus neoformans* infections is dependent on distinct Fc receptor functions and IgG subclasses", J. Exp. Med. 187:641–648.

\* cited by examiner

γ-/-
sf9   sf9-gp75

WT    WT
sf9   sf9-gp75

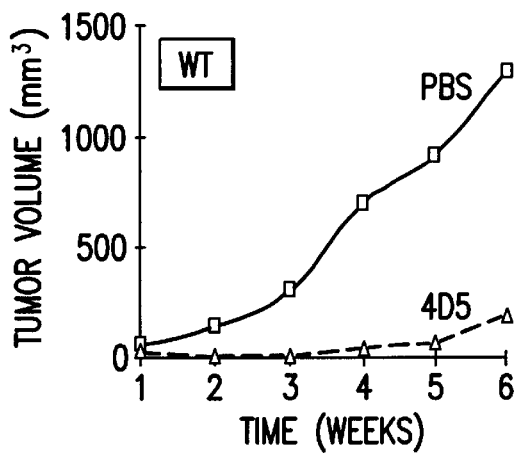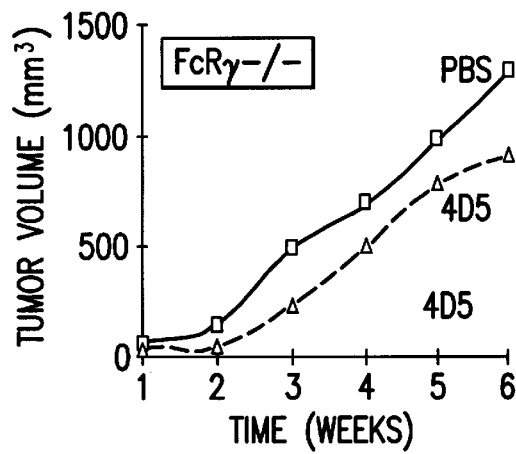
FIG.10A  FIG.10B
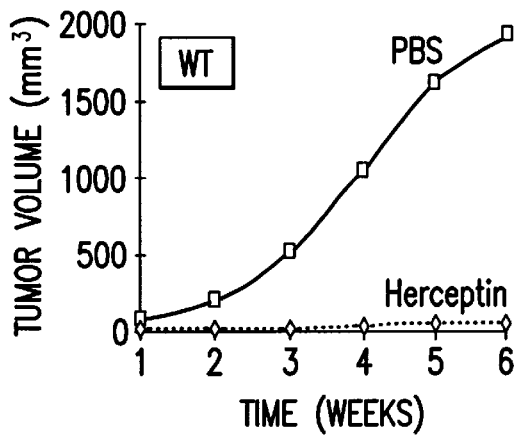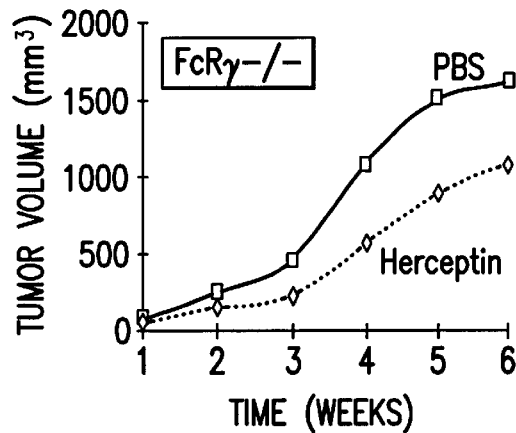
FIG.10C  FIG.10D
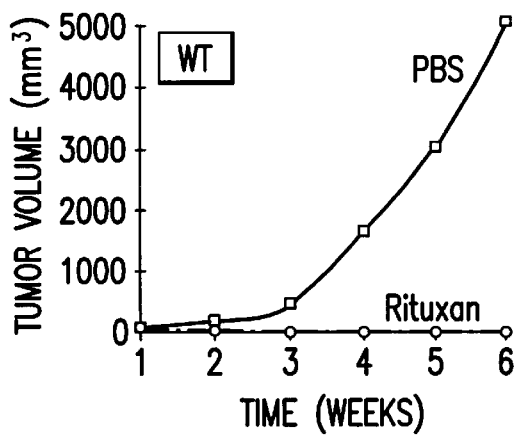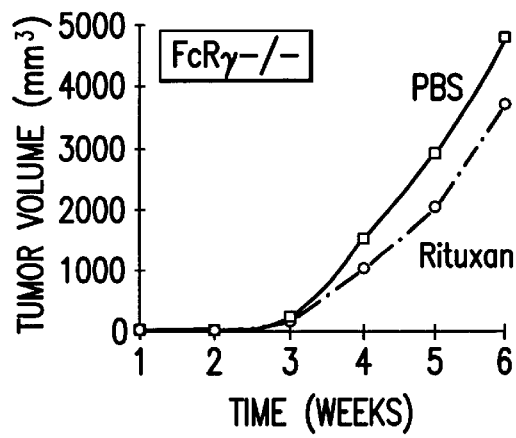
FIG.10E  FIG.10F

UNITED STATES PATENT

ANIMAL MODEL AND METHODS FOR ITS USE IN THE SELECTION OF CYTOTOXIC ANTIBODIES

This application claims benefit to provisional application No. 06/116,972, filed Jan. 20, 1999.

The invention of the instant application was made in part with government support under Grant numbers AI 35875 and CA 80757 awarded by the Department of Health and Human Services. The government has certain rights in the invention.

1. INTRODUCTION

The present invention relates to non-human animals and in vivo methods for testing the efficacy of antibodies directed to antigens expressed by tumors in such animals. In particular, the invention relates to an animal deficient in the expression of one or more Fc receptors. Additionally, such an animal is also immunodeficient, and thus permits the growth of a xenogeneic tumor implant. More specifically, an animal of the invention can be implanted with a human tumor and treated with an antibody directed to an antigen expressed by the tumor, and the anti-tumor efficacy of the antibody is compared between animals with or without Fc receptor expression. The present invention also relates to methods of evaluating the enhanced ability of an existing antibody or Fc-modified antibody to act as an immunotherapeutic to eradicate tumor cells or infectious agents.

2. BACKGROUND OF THE INVENTION

Effective immunity against cancer requires the specific recognition and elimination of malignant cells expressing targeted antigens. Antigens recognized on neoplastic cells include viral proteins, products of altered or mutated genes, developmentally reactivated silent gene products, and differentiation antigens expressed by tumor cells and their normal cell counterparts (Houghton, A. N., J. Exp. Med. 180:1 (1994); Jaffee, E. M. & Perdoll, D. M., Curr. Opin. Immunol. 8:622 (1996)). Much of the current effort of vaccine strategies is aimed at eliciting cytolytic T cell responses in which antigen recognition and cytotoxicity are functions shared by a single cell. In antibody-mediated cytotoxicity, however, antigen recognition and cytotoxicity mechanisms are functional properties of distinct cell types.

Therapeutic approaches to generate antigen-specific immune responses against tumors have included both passive immunization with monoclonal antibodies (mAbs) or adoptively transferred activated immune cells, and active immunization using antigens or genes expressing antigens. Passive immunity with antibodies could mediate its cytotoxic effects through complement activation or Fc receptor (FcR) engagement, and immunization with tumor antigens could elicit both cytolytic T cell responses and antibodies capable of triggering effector mechanisms.

Three classes of Murine FcRs for IgG1, IgG2a, and IgG2b have been characterized: the high-affinity receptor FcγRI and the two low affinity receptors FcγRII and FcγRIII (Ravetch, J. V., Curr. Opin. Immunol. 9:121 (1997)). A similar distribution exists in humans, where two genes encode FcγRIII, A and B, and three genes encode FcγRII, A, B and C (Ravetch, J. V., Curr. Opin. Immunol. 9:121(1997)). Human FcγRIIA and IIC are activating receptors, while IIB, as in mice, is an inhibitory FcR. FcγRI and III are heterooligomeric receptors, requiring co-expression of the common γ chain for their assembly and signaling functions. Cross-linking these receptors results in cell activation. FcγRIIB, in contrast, is a single chain inhibitory receptor, aborting activation through immune receptor tyrosine-based activation motif (ITAM)-containing receptors. In addition, a distinct Fc receptor for mouse IgG3 has been described (Diamond, B. & Yelton, D. E., J. Exp. Med. 153:514 (1981); Yuan, R. et al., J. Exp. Med., 187:641–648 (1998)). Mice containing genetic disruptions of the γ chain do not express either FcγRI or III and exhibit functionally impaired antibody-mediated responses, including loss of natural killer (NK) cell-mediated antibody-dependent cellular cytotoxicity (ADCC), macrophage phagocytosis, and mast cell degranulation in response to FcR cross-linking (Takai, T. et al., Cell 76:519 (1994)). Furthermore, γ chain deficiency ameliorates the pathogenesis of cytotoxic antibody in models of autoimmune hemolytic anemia and thrombocytopenia (Clynes, R. et al., J. Exp. Med. 184:2385 (1996); Clynes, R. & Ravetch, J. V., Immunity 3:21 (1995)) and the inflammatory cascade initiated by immune complexes in the Arthus reaction (Clynes, R. et al. (1996), supra; Sylvestre, D. L. & Ravetch, J. V., Science 265:1095 (1994)) and autoimmune glomerulonephritis (Clynes, R. et al., Science, 279:1052–1054 (1998); Suzuki, Y. et al., Kidney Int. 54:1166–1174 (1998)). Similar results were observed in FcγRIII 2- animals, Hazenbos, W. L., et al., 1996, Immunity 5: 181–188. Conversely, animals deficient in the inhibitory FcR, FcγRIIB, exhibit enhanced inflammatory responses to IgG antibodies or IgG immune complexes (Takai et al., Nature 379:346–349 (1996); Clynes et al., J. Exp. Med. 184:2385 (1996); Suzuki et al., Kidney Int. 54:1166 (1998)). However, selection of antibodies for use as therapeutics has focused on in vitro assays for growth inhibition, complement activation or other effector responses. These assays have not considered the in vivo activities which may be mediated by FcR dependent pathways.

3. SUMMARY OF THE INVENTION

The present invention relates to animals deficient in both immune function and FcR expression or function. Such animals permit the growth of a xenogeneic tumor implant for testing the efficacy of an anti-tumor antibody in vivo. In addition, the mouse FcR may be replaced by its human counterpart. The invention also relates to methods of using such animals in selecting antibodies that mediate anti-tumor ADCC through Fc receptor binding to effector cells. The present invention also relates to methods of evaluating the enhanced ability of an existing antibody or an Fc-modified antibody to act as an immunotherapeutic to eradicate tumor cells or infectious agents.

The invention is based, in part, on the discovery that successful active immunization with a tumor antigen and passive immunotherapy with an anti-tumor antibody in a mouse melanoma model both require the expression of FcR in the tumor-bearing host. In other words, FcR-expressing effector cells are needed to mediate optimal anti-tumor immune responses. Absence of the activating FcγR reduces antibody efficacy, while the absence of the inhibitory FcγR enhances antibody efficacy. In addition, both murine and humanized anti-tumor antibodies are effective in causing regression of a human tumor implants in nude mice, whereas the antibodies display much less effective anti-tumor activities in the same animals that are also deficient in activating FcR expression, while displaying enhanced anti-tumor activity in mice deficient in inhibitory FcR expression.

It is an object of the invention to construct a non-human immunodeficient animal which is also deficient in FcR expression or FcR function.

It is also an object of the invention to construct a non-human immunodeficient animal which expresses human FcR instead of its native FcR.

It is another object of the invention to use the aforementioned animals to select an anti-tumor antibody that mediates superior anti-tumor activities in an animal that expresses FcR as compared to an animal that lacks FcR expression. More specifically, the invention relates to a method for selecting an anti-tumor antibody comprising: (a) administering an antibody to a first non-human immunodeficient animal which is implanted with a human tumor; (b) administering said antibody to a second non-human immunodeficient animal which is implanted with said human tumor and said second animal is also deficient in Fc receptor expression or Fc receptor function; and (c) determining the ability of said antibody to retard tumor implant growth in the animal of step (a) as compared to the animal of step (b).

The present invention also relates to a method for selecting an anti-tumor antibody comprising: (a) administering an antibody to a first non-human immunodeficient animal, which is implanted with a human tumor; (b) comparing anti-tumor activity of antibody in step (a) to anti-tumor activity of antibody administered to a second non-human immunodeficient animal which is implanted with said human tumor and second animal expresses human Fc receptor or human Fc receptor function in place of murine receptors; and (c) determining the ability of said antibody to retard tumor implant growth in the animal of step (a) as compared to the animal of step (b).

It is yet another object of the invention to use a non-human FcR deficient animal to select an antibody against an infectious agent. More specifically, the invention relates to a method for selecting an anti-infectious disease agent antibody comprising: (a) administering an antibody to a first non-human animal which is inoculated with an infectious agent; (b) administering an antibody to a second non-human animal which is inoculated with said infections agent and said second animal is deficient in Fc receptor expression or Fc receptor function; and (c) determining the ability of said antibody to inhibit an activity of said infectious agent in the animal of step (a) as compared to the animal of step (b).

4. BRIEF DESCRIPTION OF THE DRAWINGS

Figure 1B:
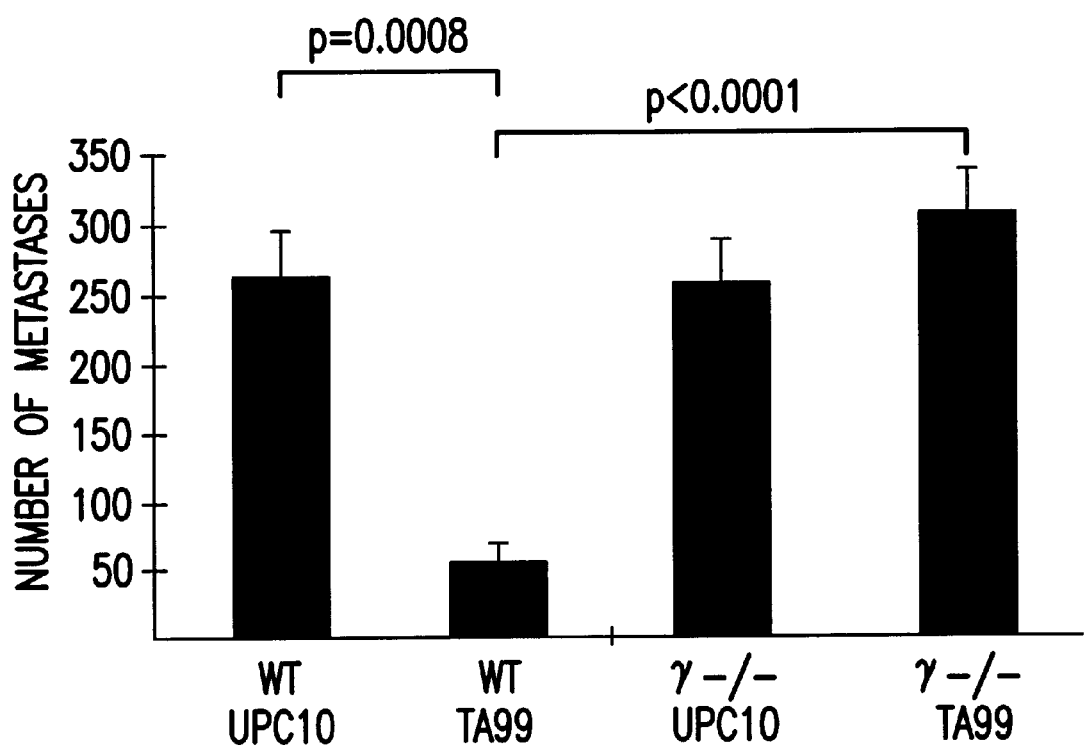

FIGS. 1A and 1B. Passive protection from melanoma metastasies requires FcRs. Six mice were present in each group. Representative lungs from the mice are shown in FIG. 1A. FIG. 1B shows P values of significant differences. UPC10 is a control isotype antibody.

Figure 2A:
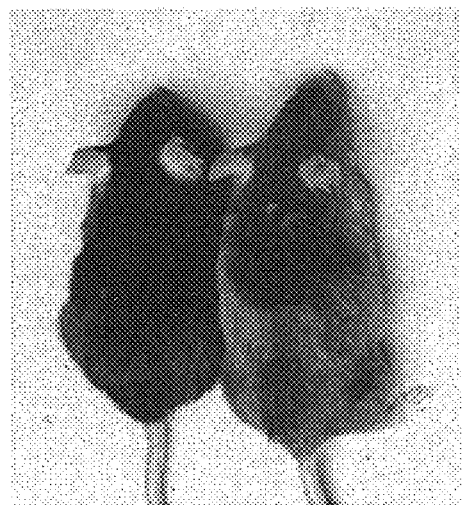
Figure 2B:
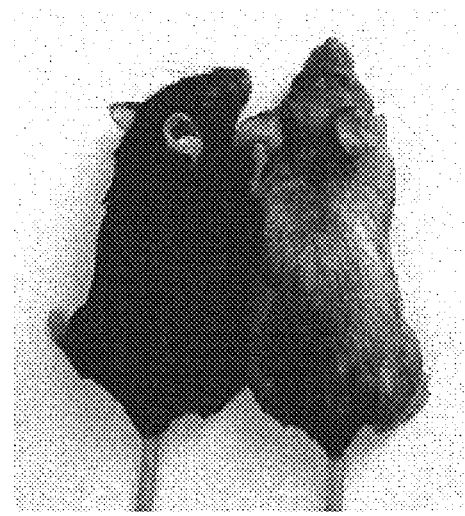

FIGS. 2A and 2B. Anti-gp75-induced depigmentation occurs normally in the FcγR-deficient mice, $\gamma^{-/-}$ (FIG. 2A) and wild type (FIG. 2B) mice were immunized with Sf9-gp75 or with control Sf9 extract.

Figure 3A:
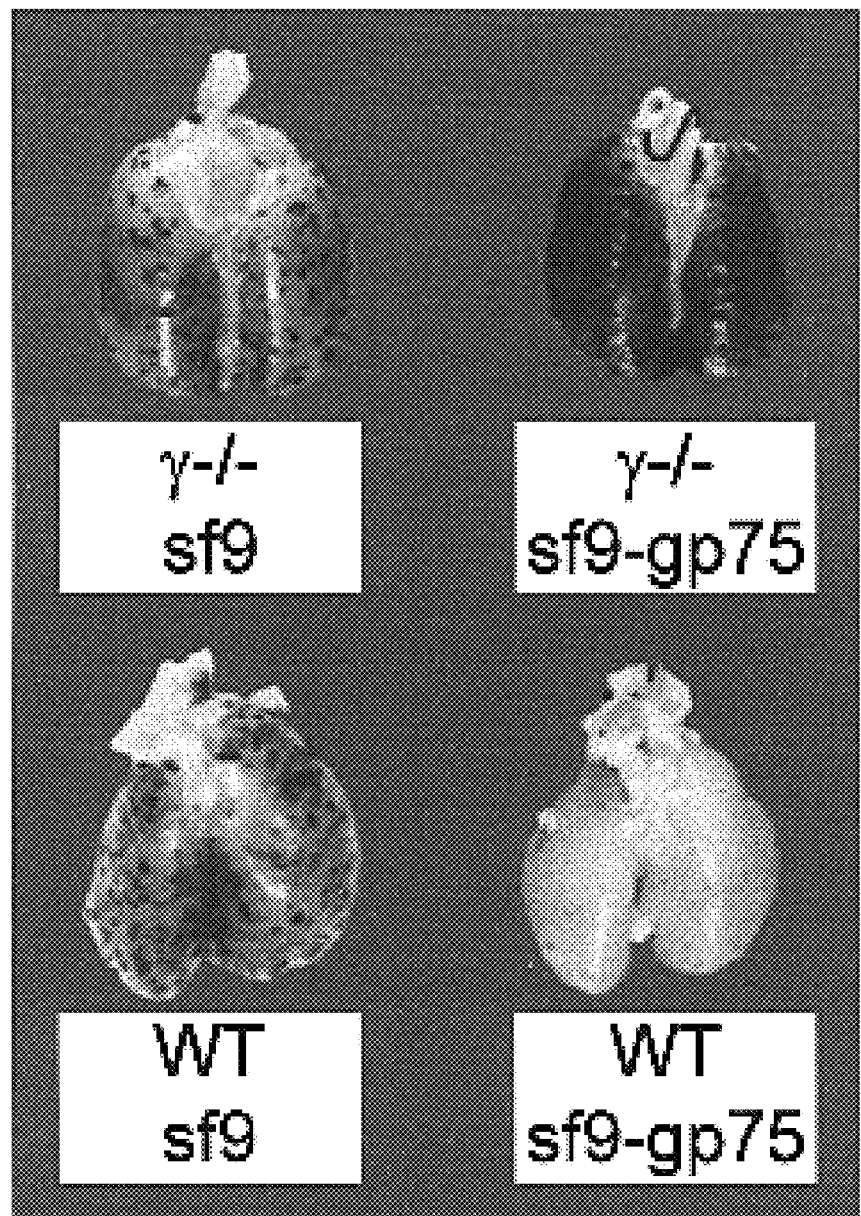
Figure 3B:
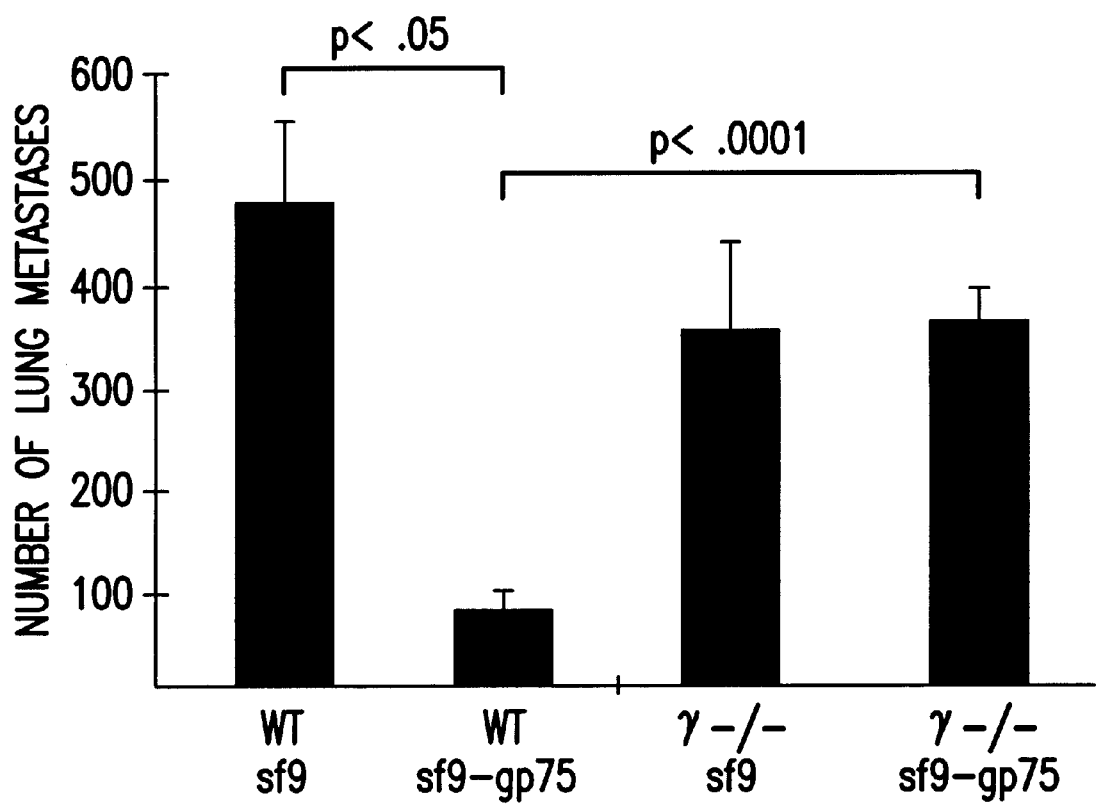

FIGS. 3A and 3B. Active protection from melanoma metastases requires FcRs.

Figure 4:
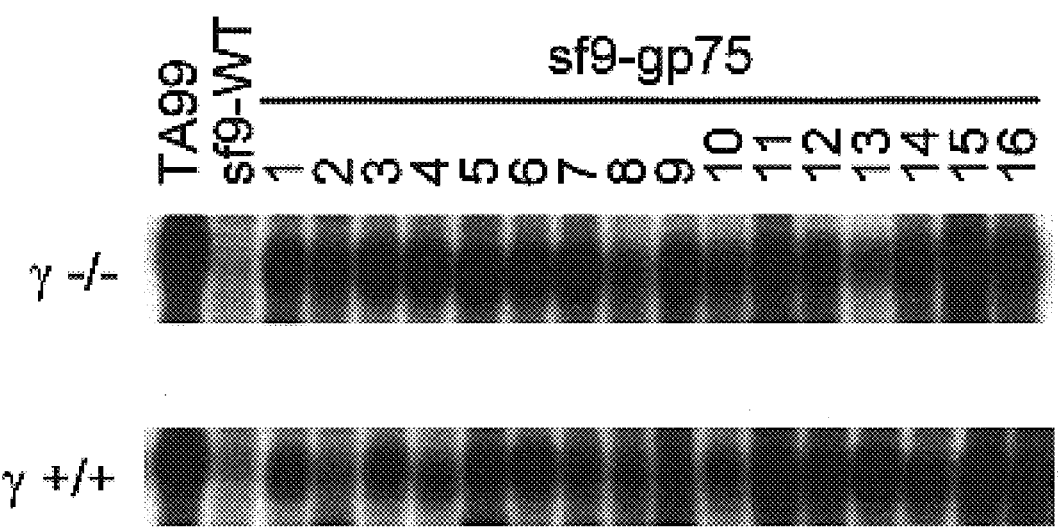

FIG. 4. Anti-gp75 titers in Sf9-gp75-immunized $\gamma^{+/+}$ and $\gamma^{-/-}$ mice are indistinguishable. Diluted TA99 mAb is positive control.

Figure 5:
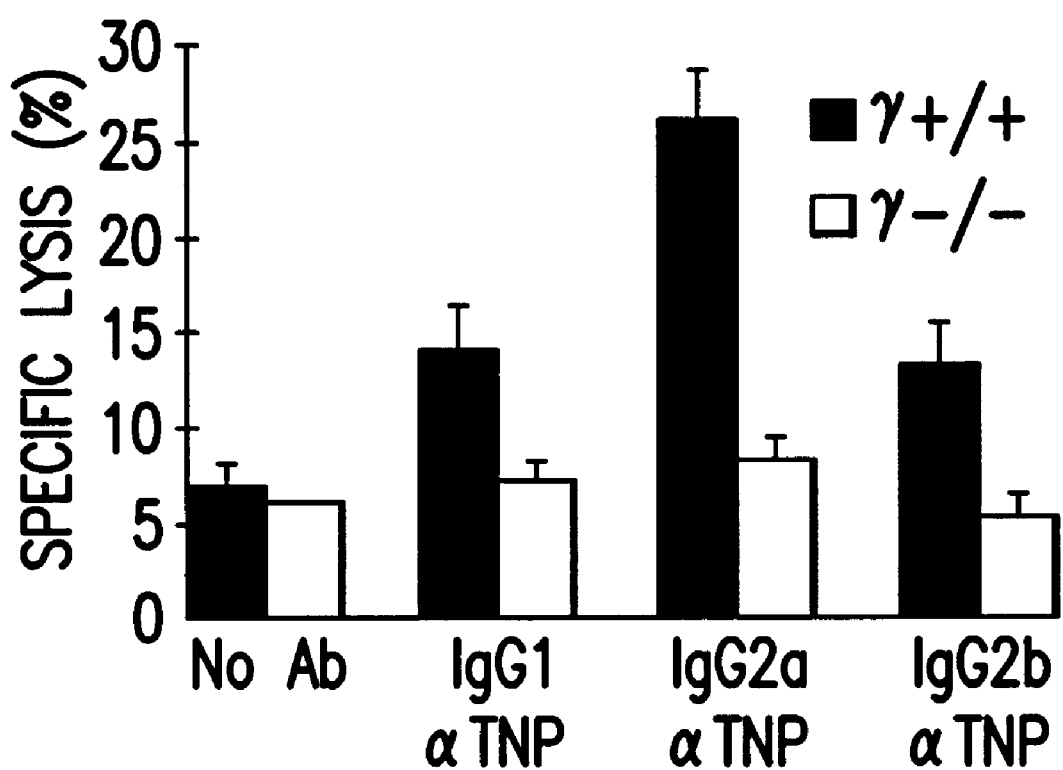

FIG. 5. Macrophage ADCC of tumor target-cells requires FcγR γ chain.

Figure 6:
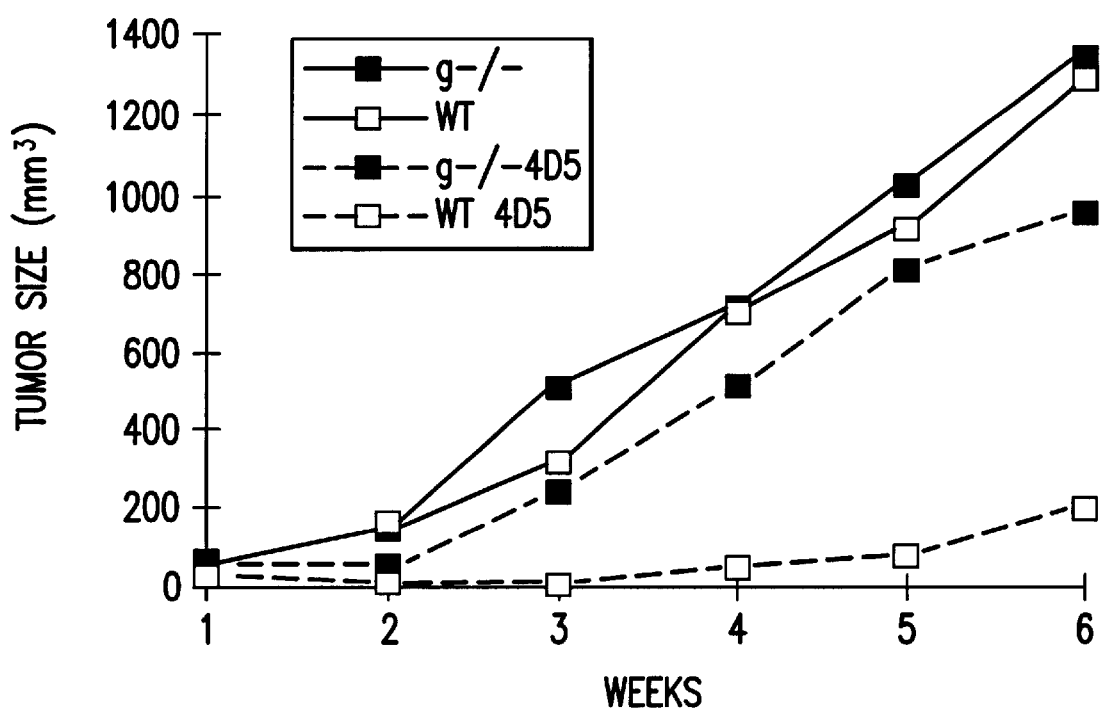

FIG. 6. Anti-HER2 monoclonal antibody, 4D5, mediates tumor cytotoxicity of human breast carcinoma implant in $\gamma^{-/-}$ nude mice, but not in $\gamma^{-/-}$ nude mice.

Figure 7:
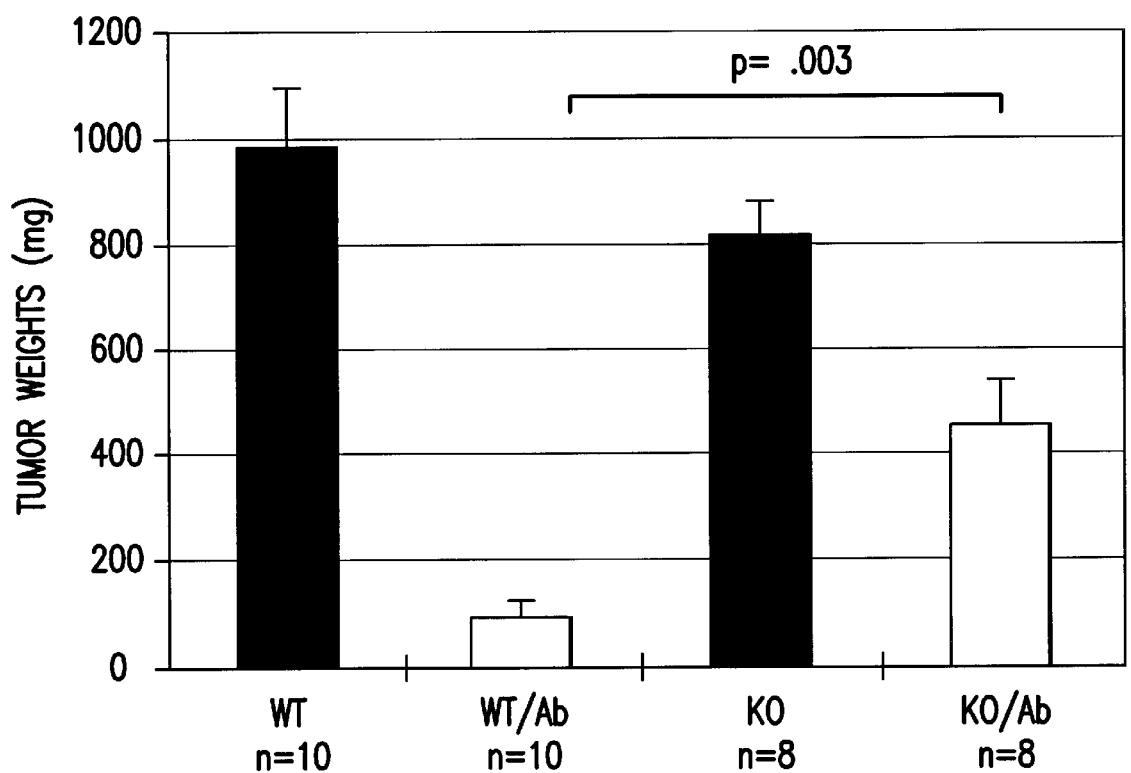

FIG. 7. Anti-HER2 monoclonal antibody, 4D5, reduces tumor weight of a human tumor implant in $\gamma^{+/+}$ nude mice, but not in $\gamma^{-/-}$ nude mice.

Figure 8:
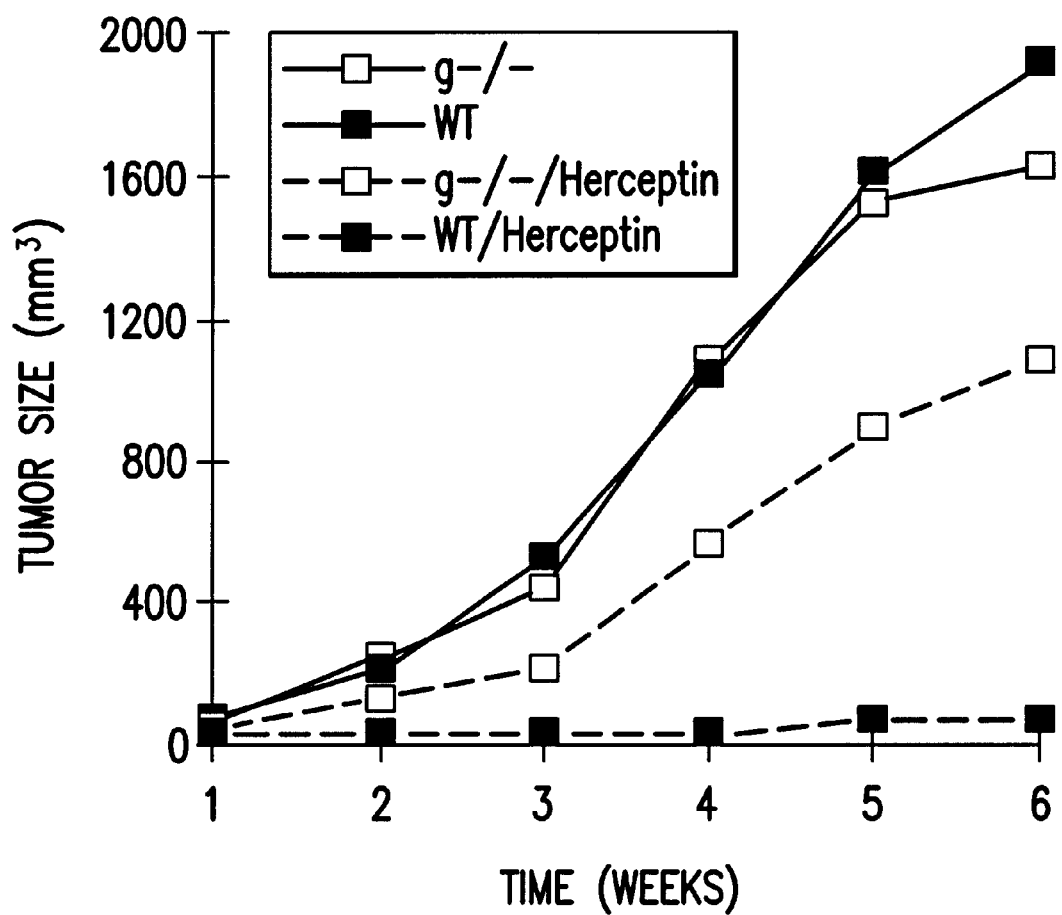

FIG. 8. Humanized anti-HER2 monoclonal antibody, HERCEPTIN®, mediates cytotoxicity of human breast carcinoma implant in $\gamma^{+/+}$ nude mice, but not in $\gamma^{-/-}$ nude mice.

Figure 9:
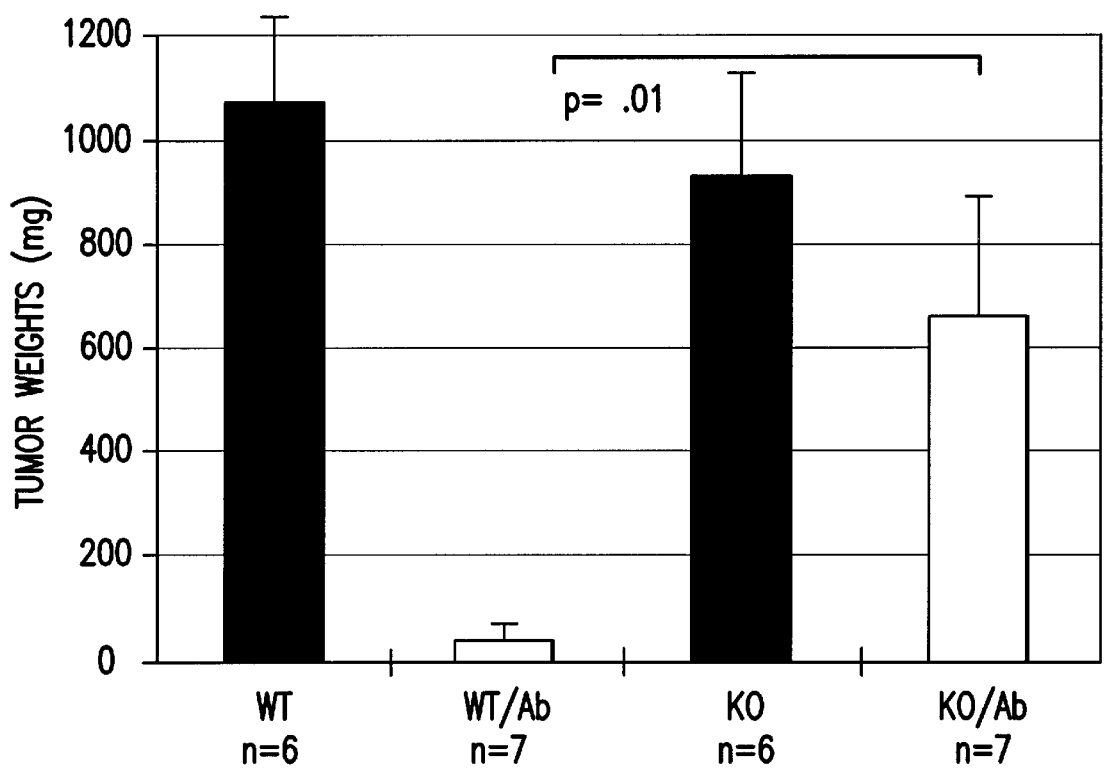

FIG. 9. Humanized anti-HER2 monoclonal antibody, HERCEPTIN®, reduces tumor weight of a human tumor implant in $\gamma^{+/+}$ nude mice, but not in $\gamma^{-/-}$ nude mice.

FIGS. 10A, 10B, 10C, 10D, 10E and 10F. Anti-tumor activity of 4D5, HERCEPTIN®, and RITUXAN® require FcγR activating receptors. Nude mice (6–10 per group) were injected subcutaneously with $5 \times 10^6$ BT474M1 cells followed by weekly injections of mAb 4D5 (FIGS. 10A and 10B) or HERCEPTIN® (FIGS. 10C and 10D) or RITUXAN® (FIGS. 10E and 10F). HERCEPTIN® antibodies were obtained from vialed clinical material (Genentech, Inc.) and given at doses consistent with clinical experience (4 μg/gm loading, 2 μg/gm weekly). RITUXAN® was obtained from IDEC Pharmaceuticals, Inc. and given at 10 μg/gm weekly. Antibody-dependent tumor protection observed in BALB/c nude mice (FIGS. 10A, 10C and 10E) is absent in FcγRγ$^{-/-}$ nude mice (FIGS. 10B, 10D and 10F). All experiments were repeated three times with similar results.

Figure 11A:
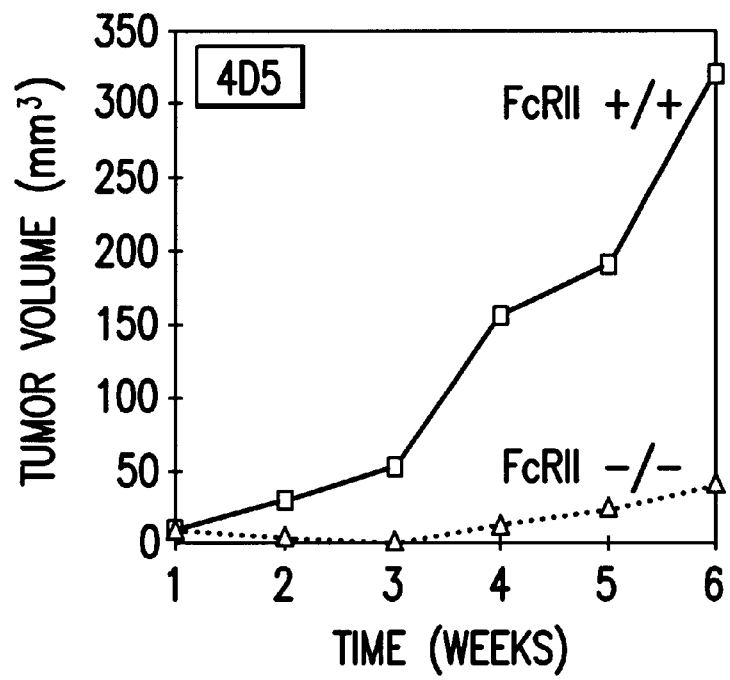
Figure 11B:
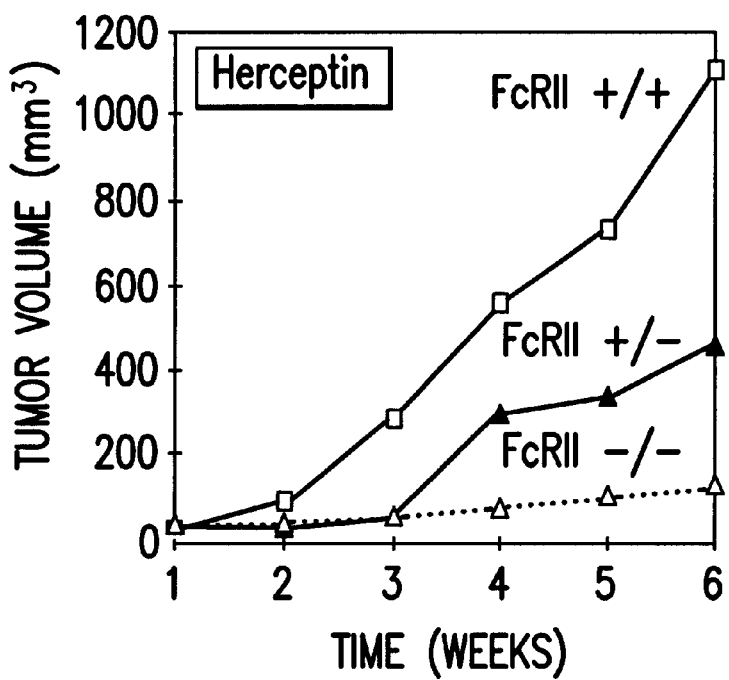

FIG. 11. Anti-breast tumor activity of 4D5 and HERCEPTIN® is enhanced in FcγRIIB deficient mice. Nude mice (8 per group) were injected with BT474M1 cells, as in FIG. 10, and treated with 0.4 μg/gm loading dose and 0.2 μg/gm weekly, a sub-therapeutic dose for wild-type mice. Complete inhibition is observed in RIIB deficient and partial inhibition in RIIB heterozygous mice.

Figure 12A:
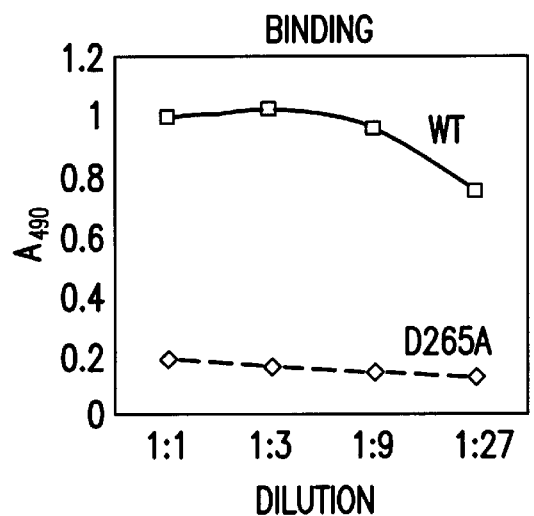
Figure 12B:
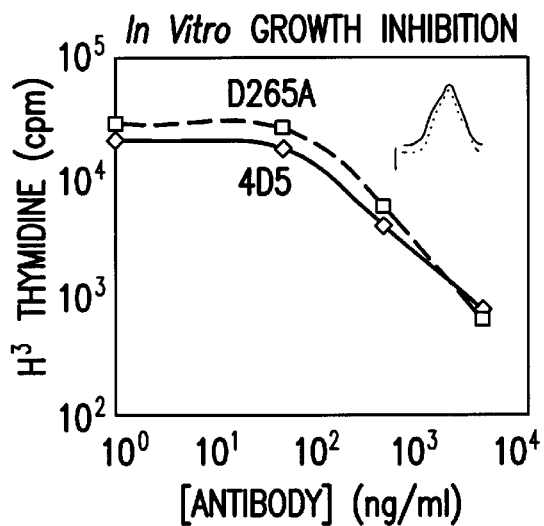

FIGS. 12A, 12B, 12C and 12D. In vitro and in vivo properties of D255A mutant antibody. (FIG. 12A) FcγRIII binding: Both wildtype and mutant Fc fragments were grafted onto an antihuman IgE Fab fragment. Solid phase binding assays were performed with human IgE/antihuman IgE hexameric complexes and recombinant FcγRIII coated plates (FIG. 12B). Growth inhibition of BT474M1 cells: (inset) FACS analysis of BT474M1 cells demonstrates equivalent avidities of 4D5 (solid line) and D265A (dotted line) for cell surface p 185HER2/neu. $^3$H-thymidine incorporation of BT474M1 cells was measured in the presence of either 4D5 or D265A antibodies. (FIG. 12C) NK cell ADCC of chromium-labeled tumor targets: Chromium labeled SKBR-3 cells were incubated with NK effector cells at varying ratios and release of label quantitated. (FIG. 12D) In vivo growth of breast carcinoma cells: Athymic BALB/c nu/nu animals were implanted with BT474M1 xenografts and their growth measured in response to treatment with 4D5, D265A or PBS.

5. DETAILED DESCRIPTION OF THE INVENTION

The challenge of cancer immunotherapy is the induction of anti-tumor immune responses specific for self or altered-self tumor antigens. The resultant immune responses are, therefore, capable of triggering both clinical tumor responses and autoimmune phenomena. In Section 6, infra, the effector mechanisms responsible for these outcomes are explored in a melanoma model in which immunization can induce both anti-tumor responses and autoimmune vitiligo. The cytotoxic response mediated by antibodies is just one possible effector mechanism contributing to the efficacy of anti-tumor mAbs or tumor vaccines. Indeed, much of the current effort in tumor immunology is directed at the generation of effective cytolytic T cell responses. In the protection model described herein, however, the critical requirement for FcγR indicates that the development of cytotoxic IgG is the dominant anti-melanoma mechanism. The results of the experiments presented herein demonstrate that the FcγR-deficient animal is a novel assay system that evaluates the role of cytotoxic IgG in immunotherapeutics.

The persistence of depigmentation induction in γ$^{-/-}$ mice reveals a distinction between the anti-tumor and anti-melanocyte effector pathways. Although antibody-mediated responses have been implicated in the pathogenesis of vitiligo (Cui, J. & Bystryn, J. C., Arch. Dermatol. 131:314 (1995); Merimsky, O. et al., Am. J. Clin. Oncol. 19:613 (1996); Fishman, P. et al., Cancer 79:1461 (1997); Hann, S. K. et al., J. Dermatol. 23:100 (1996); Merimsky, O. et al., Cancer Immunol. Immunother. 42:297 (1996); Hann, S. K. & Kim, J. B., Yonsei Med. J. 36:457 (1995); Merimsky, O. et al., Cancer Immunol. Immunother. 38:411 (1994)), the data presented herein below are more consistent with prior Thy1.2 depletion studies (Hara, I. et al., J. Exp. Med. 182:1609 (1995)) in which depigmentation was abrogated in gp75-immunized mice and suggest instead a role for T cell responses rather than cytotoxic IgG in the anti-melanocyte autoimmune response. The dissociation of depigmentation from tumor immunity in γ$^{-/-}$ mice argues that the anti-melanocyte response is not sufficient to convey tumor immunity and suggests that the clinical correlation of vitiligo with tumor responses is not necessarily the result of a shared immunological response.

The identity of the FcR-bearing effector cell that mediates the anti-gp75 cytotoxicity in tumor protection is unknown. Prior cell depletion experiments showed that both NK1.1-bearing cells and to a much lesser extent, CD4+ cells were required for TA99 protection (Hara, I. et al. (1995), supra). On the other hand, in the SCID/Beige mouse, which lacks mature T and B cells, as well as NK cells with cytolytic capacity, tumor protection by mAb TA99 is intact (Takechi, Y. et al., Clin. Cancer Res. 2:1837 (1996)), suggesting instead that cytotoxic T lymphocyte- and NK-mediated cytotoxicity are not required. These findings can be reconciled with the hypotheses that macrophage-mediated ADCC is important in anti-tumor efficacy and that CD4$^+$ and NK1.1$^+$ cells are required as immunoregulatory cells for stimulation of macrophage activity. The lack of ADCC by γ$^{-/-}$ macrophages is consistent with this hypothesis.

Regardless of the lineage of the effector cell(s) involved, the results presented herein below substantiate a critical role in vivo for FcγR-mediated ADCC in tumor immunity. Although anti-gp75-mediated ADCC has not been demonstrated in vitro, data have shown that transfer of serum from Sf9-gp75-immunized mice can protect naive mice from melanoma metastases, suggesting that serum anti-gp75 IgG is sufficient to provide protection (Naftzger, C. et al. (1996), supra; Takechi, Y. et al. (1996), supra). The evidence presented herein indicates that the FcγR effector pathway is the dominant mechanism of protection of this humoral response and is necessary for the efficacy of a tumor vaccine. Uncoupling of the FcγR pathway from antibody recognition of tumor antigens resulted in a loss of protection against tumor challenge. These observations suggest that enhancement of the functional activity of anti-tumor antibody-FcγR interactions would improve the efficacy of immunotherapeutic agents.

The identification of anti-tumor antibodies that preferentially interact with FcγR as optimal anti-tumor therapeutics is further demonstrated by the results presented herein which show that murine monoclonal antibodies, as well as the humanized, clinically effective therapeutic HERCEPTIN® and RITUXAN® engage both activation (FcγRIII) and inhibitory (FcγRIIB) antibody receptors on myeloid cells, thus modulating their cytotoxic potential. Further, mice deficient in FcγRIIB display greatly enhanced ADCC, conversely, mice deficient in activating Fc receptors, as well as antibodies engineered to disrupt Fc binding to those receptors are unable to arrest tumor growth in vivo. These results demonstrate that a general, FcR-dependent mechanism underlies the action of cytotoxic anti-tumor antibodies and that an optimal immunotherepeutic agent would bind preferentially to activation FcRs and minimally to inhibitory FcRs.

5.1 ANTIBODY Fc DOMAINS AND Fc RECEPTORS

An antibody is also known as an immunoglobulin, which is an antigen-specific secretory product of B cells. Typically, a naturally-occurring antibody is composed of two identical polypeptides referred to as heavy chains and two identical shorter polypeptides referred to as light chains. The four chains are linked by interchain disulphide linkages.

An antibody molecule has two distinct functions. Its antigen-binding region specifically binds an antigenic epitope. This portion of the antibody is known as the variable region and it consists of both the heavy and light chains. It is variable because tremendous structural diversity occurs between antibodies in this region due to their unique specificities. The other end of the antibody mediates several effector functions, and that portion of the antibody is referred to as the constant region. While there are several isotypes of antibodies due to differences in this region, the constant region does not vary to the same extent as the antigen-binding region. Upon binding to a specific antigen such as a foreign pathogen, the constant region of an antibody engages the effector functions of the immune system to dispose of the pathogen. Such biologic effector functions include complement activation, placental transfer, binding to FcR on immune cells such as macrophages and NK cells, and binding to FcR on granulocytes such as mast cells and basophils.

There are three classes of FcR that bind to the Fc portion of an antibody, which is located in its constant region. The high affinity FcγRI and two low affinity receptors FcγRIIB and FcγRIII are expressed on different cell types. The FcγRIII (CD16) is expressed on NK cells, macrophages, mass cells and neutrophils, and it is considered the most important FcR for ADCC because occupation of this receptor triggers an activation signal in the cells. The FcγRI is also an activation receptor. Thus, in order to eliminate effector cells capable of mediating ADCC in an animal, it is important to reduce the expression or function of these receptors, particularly FcγRIII. In contrast, the FcγRIIB is an inhibitory receptor which attenuates the action of FcγRIII.

5.2 CONSTRUCTION OF IMMUNODEFICIENT ANIMALS WITH ALTERED Fc RECEPTOR EXPRESSION

For the practice of the invention, the anti-tumor activities of an antibody are tested in two groups of genetically identical animals which differ only in FcR expression or function. In the first group, the animals express normal FcR, and an anti-tumor antibody that mediates ADCC is expected to retard tumor growth in these animals. In the second group, the animals are deficient in the expression or function of at least one class of FcR. In such animals, an antibody cannot mediate ADCC to result in effective anti-tumor activities. While an animal suitable for use in the invention may have a deficiency in all FcR expression or function, it is preferred that the deficiency is in FcγR I and III. More preferably, the animals deficient in activating receptors are FcγRIII deficient, alternatively, deficiency in the inhibitory FcR mediates enhanced ADCC. Such deficiencies may arise naturally as a genetic mutation or deletion, or they may be induced by genetic manipulations of animals using gene knock-out techniques that target the FcR genes. Such techniques are well known in the art. Animals with various FcR deficiencies are available from commercial sources such as The Jackson Laboratory (Bar Harbor, Me.) and Taconic Farms (Germantown, N.Y.).

In order for the aforementioned animals to maintain a xenogeneic tumor implant, an animal suitable for use in the present invention is also immunodeficient. For the purpose of this invention, an immunodeficient animal is not capable of mounting an immune response that results in the rejection of a xenogeneic tumor implant. Such immunodeficiency may affect certain specific immune compartments of an animal such as T cell deficiency as manifested in athymic nude mice or deficiencies that affect multiple compartments such as severe combined immunodeficiency as manifested in scid mice and rag mice.

An immunodeficient animal that is defective in FcR expression or function can be implanted with a human tumor and tested as an in vivo model for the efficacy of an anti-tumor antibody as compared to animals that express normal FcR. While such an animal may be created by gene knock-out techniques which target FcR genes and genes that affect immune functions, it can be more readily constructed by intercrossing an immunodeficient animal with an animal with FcR deficiency, and bred for several generations. In a preferred embodiment of the invention illustrated by examples in Section 8, infra, an immunodeficient animal is rendered deficient in expressing its own FcR, and a human FcR transgene is introduced, so that the animal expresses human FcR instead of mouse FcR. In such an animal, an anti-tumor antibody can be tested for its ability to interact with human FcR-expressing effector cells, thus providing information directly predictive of the activities of the antibody in human patients. However, as shown in the working example in Section 7, infra, both a mouse monoclonal antibody and its humanized version are capable of mediating ADCC in mice by interacting with mouse FcR-expressing cells, indicating that mouse and human antibodies exhibit cross-species cross-reactivity with FcR-expressing effector cells.

While a number of non-human animals may be constructed for the practice of the invention, including but not limited to, mice, rats, hamsters and rabbits, mice are preferred because of their ease of handling and the large number of available reagents. Many different existing strains of mice with altered FcR I, FcR II, or FcR III expression have been described. These include: (C57BL/6cx129)-[KO]FcεRIγ (Takai, T. et al., Cell 76:519 (1994)); (C57BL/6J)-[KO] FcεRIγ N12 (Clynes, R. et al., Proc. Natl. Acad. Sci. USA 95:652 (1998)); BALB/cByJ-[KO]FcεRIγ N12 (Yuan et al., J. Exp. Med. 187:641–648(1998); (C57BL/6cx129)-[KO] FcγRII (Takai, T. et al., Nature 379:346 (1996)); (C57BL/6J)-[KO]FcγRII N12 (Taconic Farms, Germantown, N.Y.); BALB/cByJ-[KO]FcγRII N12 (Taconic Farms, Germantown N.Y.);and (C57BL/6cx129)-[KO]FcγRIII.

Similarly, a number of immunodeficient mice are also available for use in the invention. These mice, include but are not limited to, nude mice, scid mice and mice deficient in the rag-1 and rag-2 genes. Other animals with diverse types of immunodeficiency as a result of mutations of certain genetic loci can be found in the website immunology.tch.harvard.edu. These immunodeficient mice permit the growth of a xenogeneic tumor implant and may be crossed with the aforementioned FcR deficient mice to produce progenies that are deficient in both immune function and FcR expression. For example, currently existing mouse strains of this type include BALB/cByJ-Hfh11$^{nu}$-[KO] FcεRIγ; and BALB/cByJ-Hfh11$^{nu}$-[KO]FcγRIII. Additionally, immunodeficient mice expressing a human FcR transgene are also available, and they include (C57BL/6xCBA/CA)-TgN(hFcγRIIIA) (Li, M. et al., J. Exp. Med. 183:1259 (1996)); (C57BL/6x129)-[KO]FcγRIII-TgN (hFcγRIIIA); and BALB/cByJ-Hfh11$^{nu}$-[KO]FcγRIII-TgN (hFcγRIIIB).

In order to create a knock-out animal that is deficient in FcR or a transgenic animal that expresses a human FcR, any technique known in the art may be used to introduce a transgene into animals to produce the founder lines of transgenic animals. Such techniques include, but are not limited to, pronuclear microinjection (Hoppe and Wagner, 1989, U.S. Pat. No. 4,873,191); retrovirus-mediated gene transfer into germ lines (Van der Putten, et al., 1985, Proc. Natl. Acad. Sci., USA 82:6148–6152); gene targeting in embryonic stem cells (Thompson, et al., 1989, Cell 56:313–321); and electroporation of embryos (Lo, 1983, Mol. Cell. Biol. 3:1803–1814; Gordon, 1989, Transgenic Animals, Intl. Rev. Cytol. 115, 171–229). Any technique known in the art may be used to produce transgenic animal clones containing a FcR transgene, for example, nuclear transfer into enucleated oocytes of nuclei from cultured embryonic, fetal or adult cells induced to quiescence (Campbell, et al., 1996, Nature 380:64–66; Wilmut, et al., Nature 385:810–813).

The present invention provides for knock-out animals in which one or more native FcR genes have been affected (Ravetch and Clynes, Annu. Rev. Immunol. 16:421–432 (1998)). The present invention also provides for transgenic animals that carry human FcR transgene in all their cells, as well as animals that carry the transgene in some, but not all their cells, i.e., mosaic animals. The transgene may be integrated as a single transgene or in concatamers, e.g., head-to-head tandems or head-to-tail tandems. The transgene may also be selectively introduced into and activated in a particular cell type by following, for example, the teaching of Lasko et al. (1992, Proc. Natl. Acad. Sci. USA 89:6232–6236). The regulatory sequences required for such a cell-type specific activation will depend upon the particular cell type of interest, and will be apparent to those of skill in the art. When it is desired that the transgene be integrated into the chromosomal site of the endogenous FcR gene, gene targeting is preferred. Briefly, when such a technique is to be utilized, vectors containing some nucleotide sequences homologous to the endogenous FcR gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu, et al. (1994, Science 265: 103–106). The regulatory sequences required for such a cell-type specific inactivation will depend upon the particular cell type of interest, and will be apparent to those of skill in the art.

Once transgenic animals have been generated, the expression of the recombinant gene may be assayed utilizing standard techniques. Initial screening may be accomplished by Southern blot analysis or PCR techniques to analyze animal tissues to assay whether integration of the transgene has taken place. The level of mRNA expression of the transgene in the tissues of the transgenic animals may also be assessed using techniques that include, but are not limited to, Northern blot analysis of tissue samples obtained from the animal, in situ hybridization analysis, and RT-PCR. Samples of FcR gene-expressing cells, may also be evaluated immunocytochemically using antibodies specific for FcR.

5.3 IN VIVO SELECTION OF ANTI-TUMOR ANTIBODIES

The experimental results presented in Sections 6 and 7, infra, show that an antibody directed to an antigen expressed by tumor cells can cause tumor regression by ADCC through binding to FcR-expressing immune effector cells. In fact, the data presented in the working examples below show that ADCC may represent an important mechanism in vivo for tumor eradication in both active and passive tumor immunotherapy. As such, an antibody may be used therapeutically in humans without being conjugated to a toxin, a radioisotope or a drug. Furthermore, an antibody that does not activate complement effectively may still interact with FcR to mediate ADCC of tumors, since complement fixation and ADCC depend on different structural regions of an antibody Fc domain.

In a specific aspect of the invention, an antibody is administered in an animal with a human tumor implant, and tested for its ability to retard in vivo tumor growth. In that connection, an anti-tumor antibody of any species may be selected in such an animal model. Such antibodies include, but are not limited to, human antibodies, rodent antibodies, hamster antibodies and rabbit antibodies. Murine antibodies are preferred since the vast majority of antibodies directed to human tumor antigens are of murine origin. In addition, the antibodies may be polyclonal, monoclonal or chimeric (e.g., humanized). In one embodiment, a chimeric antibody may be made by splicing the genes from a mouse antibody molecule of appropriate antigen specificity together with genes from a human antibody molecule of appropriate biologic activity (U.S. Pat. Nos. 4,816,567 and 4,816,397). A humanized antibody is a chimeric antibody which may be made by splicing the genes encoding the complementarity-determining regions of a mouse antibody together with variable region framework region and constant region genes from a human antibody molecule (U.S. Pat. Nos. 5,693,762, 5,585,089, 5,565,332 and 5,821,337). An antibody suitable for testing in the present invention may be obtained from natural sources or produced by hybridoma, recombinant or chemical synthetic methods, including modification of constant region functions by genetic engineering techniques (U.S. Pat. No. 5,624,821). The antibody may be of any isotype, especially human IgG1 and IgG3.

For testing the antibody in vivo, the animal is implanted with a xenogeneic tumor such as human tumor. The cell dose for each tumor varies, but can be readily determined by one skilled in the art in titration experiments. It is preferred that the cell dose does not cause death of the tumor bearing hosts for at least 2 weeks. It is more preferred that the cell dose does not cause death for at least 6–8 weeks, so that the efficacy of a test antibody can be determined over a sufficient time period. While the tumor cells may be implanted in a host animal by any route of inoculation, including but not limited to, subcutaneous, intradermal, intravenous, intramuscular, intraperitoneal, intraocular, subcutaneous tumor inoculation is preferred because tumor growth can be readily monitored visually or measured by a caliper.

A test antibody may be formulated in aqueous solutions for administration, preferably in physiologically compatible buffers, such as Hank's solution, Ringer's solution or physiological saline buffer. The solution may contain formulatory agents such as suspending, stabilizing and/or dispersing agents. Alternatively, the antibody may be in power form for constitution with a suitable vehicle, e.g., sterile pyrogen-free water, before use. In addition, an antibody can be formulated as a pharmaceutical composition using one or more physiologically acceptable carriers, diluents, excipients or auxiliaries which facilitate processing of the antibody into preparations which can be used pharmaceutically.

The effective dosage of each antibody varies, and can be estimated initially from in vitro assays. It also depends on the nature of the target antigen, the density of the antigen in the tumors, the tumor type, the manner of administration, which can be optimized by a person skilled in the art without undue experimentation. Usual effective dosages for injection range from about 0.1 to 5 mg/kg/day, preferably from about 1 to 4 mg/kg/day, and more preferably from 2 to 4 mg/kg/week.

In an animal with a human tumor implant, the antibody may be administered concurrently with tumor implantation or shortly after tumor implantation. Alternatively, the antibody is administered after the implant is established, i.e., visible or palpable. Antibody infusion may be repeated on a regular basis for a period of time, preferably between 4 to 8 weeks. Death of animals may be used as an end point of the experiment. Alternatively, anti-tumor activity of an antibody is measured by tumor size during the test period or tumor weight after the animals are sacrificed at the completion of the study. The measured parameters are compared between animals that express FcR and animals that are deficient in FcR. An antibody that retards tumor growth in animals with normal FcR expression is selected as capable of mediating anti-tumor ADCC, and thus a candidate for use in human cancer patients. In the context of the invention, retardation of tumor growth includes both inhibition of further tumor growth and regression of tumor growth.

In another aspect of the invention, a FcR deficient animal may be used to select antibodies directed to infectious disease agents such as a virus, a bacterium, a fungus and a protozoan. The efficacy of an antibody in a FcR deficient animal can be compared with normal animals to determine if the antibody requires FcR-expressing effector cells for optimal activities. In that regard, the animals do not need to be immunodeficient since many infectious agents affect both human and non-human species. Alternatively, a vaccine candidate can also be tested in this animal model to determine the importance of FcR-expressing cells in active immunization.

6. EXAMPLE: Fc RECEPTORS ARE REQUIRED IN PASSIVE AND ACTIVE IMMUNIZATION AGAINST MELANOMA IN A MOUSE MODEL

The induction of immune responses to melanoma has been associated with improved clinical outcomes in melanoma patients (Livingston, P. O. et al., J. Clin. Oncol. 12:1036 (1994)). Immunotherapeutic approaches to this disease have been actively pursued. A number of differentiation antigens have been shown to be recognized by the immune system of patients with melanoma. The melanosome, a cellular organelle found in melanoma cells and normal melanocytes, expresses several glycoproteins that are potential targets for immunity (Houghton, A. N. J. Exp. Med. 180:1–4 (1994)). In particular, the product of the brown locus (protein gp75) is expressed both intracellularly and on the cell membrane by normal melanocytes and melanoma and is recognized by T cells and autoantibodies in melanoma patients (Wang, R. F. et al., J. Exp. Med.

181:799 (1995); Vijayasaradhi, S. et al., J. Exp. Med. 171:1375 (1990)). In a model of passive immunization against gp75 using B16F10 melanoma lung metastases, the mAb TA99 against gp75 is highly effective in preventing and eradicating early-established metastases (Hara, I., J. Exp. Med. 182:1609 (1995)). In a model of active immunization against gp75, mice immunized with recombinant mouse gp75 expressed in insect cells develop a high-titer anti-gp75 antibody response and are likewise protected in the B16F10 lung metastases model (Naftzger, C. et al., Proc. Natl. Acad. Sci. USA 93:14809 (1996)). In the subsections below, experiments were performed to demonstrate the contributions of FcR to the protective immune response induced against the gp75 tumor differentiation antigen in these models. The results show that the FcR-mediated effector pathway is critical in both actively and passively immunized mice for tumor rejection.

6.1 MATERIALS AND METHODS
6.1.1 Mice and Tumors

FcR γ chain-deficient mice were successively backcrossed to C56BL/6 mice (The Jackson Laboratories, Bar Harbor, Me.) for 12 generations. Six- to 8-week-old female γ chain-deficient congensis mice or wild-type (wt) C57 BL/6 (The Jackson Laboratory) were used for all experiments. The B16F10 mouse melanoma cell line of C57BL/6 origin were maintained in Eagle's MEM containing 1% nonessential amino acids, penicillin (100 gg/ml), streptomycin (100 μg/ml) and 2 mM glutamine, and supplemented with 5% heatin-activated fetal bovine serum (Sigma, St. Louis, Mo.). B16F10 melanoma cells were detached with 0.02 mM EDTA in PBS and were washed twice with PBS. Mice were injected intravenously (i.v.) through the tail vein with $10^5$ B16F10 melanoma cells in 0.2 ml of sterile PBS. Mice were sacrificed 14–17 days later and lung surface metastases were counted as black nodules under a dissecting microscope.

6.1.2 TA99 Passive Protection Model

Mice were injected intravenously with $10^5$ B 16 melanoma cells on day 0 and with 200 μg of purified TA99 antibody or control mouse IgG2a mAb UPC10 (Sigma) on days 0, 2, 4, 7, 9, and 11. TA99 (IgG2a) mAb antibodies were purified from ascites fluid by protein A chromatography (Pharmacia LKB).

6.1.3 Sf9-gp75 Active Protection Model

A recombinant baculovirus expression vector containing the full-length murine gp75 cDNA has been described (Naftzger, C. et al. (1996), supra). Cell suspensions of Sf9 cells (Invitrogen) infected with wt or recombinant murine gp75 baculovirus were harvested by scraping and lysates prepared by three successive freeze-thaw cycles. Initial intraperitoneal (i.p.) immunizations were in complete Freund's adjuvant and the subsequent three intraperitoneal immunizations at 2-week intervals were in incomplete Freund's adjuvant (Sigma). Four weeks after the last immunization serum was obtained to check antibody responses and the mice were injected intravenously through the tail vein with $10^5$ B16 melanoma cells.

6.1.4 Immunoprecipitation

Precleared sera obtained from immunized mice were mixed with [$^{35}$S] methionine-labeled B16F10 lysates ($3-10\times10^6$ cpm of trichloroacetic acid-insoluble precipitate) and pelleted with protein A-Sepharose. Disrupted complexes were subjected to denaturing PAGE and autoradiography. Purified anti-gp75 mAb TA99 was used as a positive control.

6.1.5 Macrophage-Mediated ADCC

Peritoneal macrophages were obtained from mice immunized with live attenuated bacillus Calmette-Guérin (Organon Teknika-Cappel) subcutaneously in complete Freund's adjuvant followed by i.p. administration 6 weeks later. Approximately $10^7$ macrophages were obtained per animal 7 days after i.p. inoculation. Macrophages were cultured at an effector/target ratio of 10:1 ($10^5$ effector to $10^4$ target cells per well) in 96-well plates. Target cells were chromium-51-labeled HSB-2 lymphoma cells derivitized with 2,4,6 trinitrophenyl (TNP) and opsonized with subagglutinating quantities of anti-TNP hybridoma supernatants. TNP-specific hybridomas included TIB191 (IgG1) obtained from the American Type Culture Collection. ADCC reactions were for 6 h and specific activities were obtained as [(cpm from cultures with antibody)–(cpm from cultures with medium)/(total cpm)]. Samples were assayed in triplicate with results expressed as the mean± SEM.

6.2 RESULTS
6.2.1 FcR Is Required for Passive Protection of Melanoma Metastases by mAb TA99.

To determine the in vivo consequences of the loss of FcγRs in tumor immunity, $\gamma^{-/-}$ congensis mice were developed by 12 successive backcrosses to the FcR $\gamma^{-/-}$ background (129/B31.6). To show that the genetic background of the congensis line was phenotypically similar to C57BL/6 mice, C57BL/6$\gamma^{+/-}$ heterozygous mice were compared with wt C57BL/6 mice for baseline susceptibility to lung metastases in the B16F10 melanoma model. The number of lung metastases in congensis $\gamma^{+/-}$ mice were found to be similar to wt C57BL/6 mice (195±15 vs. 187±20 nodules). In addition, both strains were similarly protected from lung metastases by passive immunization with mAb TA99 against gp75 (85% vs. 78% reduction). Deletion of FcγRI and -III by disruption of the common γ chain, however, results in loss of the protective effect of TA99, as shown in FIG. 1A and 1B, indicating that FcγR effector pathways are necessary for tumor rejection in mice passively immunized with mAb TA99.

6.2.2 FcR Is Required for Protection of Melanoma Metastases by Active Vaccination.

In comparison with passive immunization, the situation in actively immunized mice is far more complex and is expected to include the polyclonal induction of both anti-gp75 T cells and antibodies, thus providing the host a number of possible cytotoxic effector systems including both cytotoxic T lymphocyte-mediated and antibody-mediated pathways. To determine the importance of the antibody-mediated FcγR effector pathway in actively immunized mice, $\gamma^{-/-}$ and wild-type (wt) mice were immunized with syngeneic gp75 expressed in cellular extracts of insect cells infected with mouse gp75 baculovirus constructs or with wt Sf9 cellular extracts. One consequence of Sf9-gp75 immunization is the induction of auto immune depigmentation. This coat-color change recapitulates a possible clinical association of prolonged survival and vitiligo in melanoma patients (Nordlund, I. J. et al., Am. Acad. Dermnatol. 9:689 (1983); Duhra, P. & Ilchyshyn, A., Clin. Exp. Dermatol. 16:303 (1991); Cui, J. & Bystryn, J. C. (1995), supra; Merimsky, O. et al., Am. J. Clin. Oncol. 19:613 (1996); Rosenberg, S. A. & White, D. E., J. Immunother. Emphasis Tumor Immunol. 19:81 (1996)). The typical appearance of depigmentation occurred in both wt and $\gamma^{-/-}$ Sf9-gp75-immunized mice, indicating that the effector arm of the anti-melanocyte immune response, probably T cell-mediated (Hara, I. et al. (1995), supra), does not require an intact FcγR γ chain (FIGS. 2A and 2B).

Distinct from this autoimmune phenomenon, the anti-tumor effects of Sf9-gp75 immunization were strikingly different in the two strains of mice. Consistent with prior studies, Sf9-gp75-immunized wt mice had a significant reduction in lung metastases, with 83% fewer nodules (FIG. 3A and 3B). In contrast, Sf9-gp75-immunized $\gamma^{-/-}$ mice were afforded no protection against melanoma metastases. $\gamma^{-/-}$ mice have been shown to have normal immune responses to a variety of antigenic challenges (Takai, T. et al. (1994), supra; Vora, K. A. et al., J. Immunol. 159:2116 (1997)). This same situation is seen in the $\gamma^{-/-}$ congensis mice used in these studies because easily detectable anti-gp75 IgG were found in Sf9-gp75-immunized wt and $\gamma^{-/-}$ mice (FIG. 4). Immunized $\gamma^{-/-}$ congensis mice exhibited normal CD4 and CD8 T cell responses when immunized with PCC (pigeon cytochrome c) peptide and OVA (ovalbumin) peptide, respectively. Class II-restricted T cell proliferative responses of $CD4^+$ lymph node cells from wt and $\gamma^{-/-}$-immunized mice were comparable when cocultured with PCC peptide. Both wt and $\gamma$-deficient splenocytes were capable of T cell-mediated OVA-specific killing of OVA-pulsed EL-4 target cells at comparable effector/target ratios, thereby demonstrating that the cytolytic $CD8^{+T}$ cell response is unaltered in $\gamma$-deficient mice. Thus, these experiments demonstrate that both T cell immune recognition (anti-PCC response) and effector responses (anti-OVA-pulsed EL-4 cytotoxicity) are intact in $\gamma^{-/-}$ mice. Despite the fact that these mice are capable of developing normal B and T cell immune responses, the genetic disruption of the $\gamma$-mediated effector pathway is sufficient to abrogate the efficacy of a tumor vaccine. In the absence of Fc$\gamma$R, a requisite receptor for antibody-mediated tumor cytotoxicity, anti-melanoma responses are rendered incapable of tumor protection.

6.2.3 MacrophageMediated ADCC Is Abolished in $\gamma^{-/-}$ Mice

To determine the mechanism by which FcR-deficient mice are unable to mediate an ADCC response, FcR-expressing effector cells were studied in vitro. Both NK cells and myeloid cells express FcRs and are capable of antibody-mediated tumor cytotoxicity. In vitro data has indicated that ADCC mediated by NK cells, which express only the type III Fc$\gamma$R, is abolished in $\gamma$-chain deficient mice (Takai, T. et al. (1994), supra). It is unlikely that only NK cells are involved in ADCC in the B16 murine melanoma model, because studies have shown (Takechi, Y. et al. (1996), supra) that SCID/Beige mice, which lack NK cytolytic capacity, are capable of sustaining a TA99-mediated protective response. To ascertain whether macrophages, which express all three Fc$\gamma$Rs, also require the $\gamma$ chain for anti-tumor ADCC, bacillus Calmette-Guérin-activated peritoneal macrophages were cocultured with TNP-derivitized HSB-2 tumor target cells in the presence of anti-TNP antibodies. Unlike the situation with TA99 and B16F10 tumor target cells (Naftzger, C. et al. (1996), supra; Takechi, Y. et al. (1996), supra), this system efficiently produces ADCC reactions. Whereas wt macrophages killed 27% of IgG2a-opsonized HSB-2 tumor cells, there was no enhancement of $\gamma^{-/-}$ macrophage-mediated cytotoxicity with IgG1, IgG2a, or IgG2 b opsonization (FIG. 5). Therefore, both NK and monocyte lineage effectors require the $\gamma$ chain for effective ADCC of tumor target cells in vitro, suggesting that both cellular populations may be significant in tumor immunity and thus compromised in $\gamma^{-/-}$ mice.

7. EXAMPLE: AN ANTIBODY SPECIFIC FOR A HUMAN TUMOR ANTIGEN REQUIRES Fc RECEPTOR BINDING TO MEDIATE CYTOTOXICITY IN VIVO

7.1 MATERIALS AND METHODS
7.1.1 Transgenic Mice, Tumors and Antibodies

Mice were generated by intercrossing BALB/cByJ-Hfh11$^{nu}$ immunodeficient mice (Jackson Laboratories, Bar Harbor, Me.) with BALB/cByJ-[KO]FC$\epsilon$RI$\gamma$N12 (Taconic Farms, Germantown, N.Y.) mice that were deficient in the FcR $\gamma$ chain. F1 animals were backcrossed to BALB/cBy-Hfh11$^{nu}$ mice. F2 animals were self-mated to generate the strain.

Mice of the indicated genotype were deficient in T cells and Fc$\gamma$RI and III expression, and they were implanted with $5 \times 10^6$ BT474 human breast carcinoma cells subcutaneously. Animals were either left untreated, or were treated with a murine anti-HER 2 antibody 4D5 (U.S. Pat. No. 5,677,171 issued on Oct. 14, 1997) or humanized 4D5 known as humAb4D5-8; or HERCEPTIN® (Carter et al., 1992, Proc. Natl. Acad. Sci. USA 89:4285–4289; U.S. Pat. No. 5,821,337 issued on Oct. 13, 1998) or a chimeric antibody specific for the B cell marker CD20 known as RITUXAN® (Maloney et al., 1997, J. Clin. Oncol.15:3266; Legel et al., 1998, Curr. Opin. Oncol. 10:548; Maloney et al., 1997, Blood 90:2188; Nguyen et al., 1999, Eur. J. Haematol 62: 76; Coiffier et al., 1998, Blood 92:1927; McLaughlin et al., 1998, J. Clin. Oncol. 16:2825). For antibody-treated animals, a loading dose of 4 mg/kg of antibody was given intravenously at the time of tumor implantation, followed by 2 mg/kg i.v. weekly for six weeks. Tumor sizes were measured by calipers weekly and volumes calculated. After six weeks, mice were sacrificed, the tumors excised and their weights determined.

7.2 RESULTS

Human breast carcinoma xenografts were introduced into BALB/C ByJ-Hfh11 $^{nu}$ nude mice and $\gamma^{-/-}$ nude mice, which were either untreated or were treated with an antibody against breast tumor antigen, HER2, over a period of six weeks. Untreated animals showed increases in tumor growth such that maximum tumor size was 1400 mm³ over six weeks (FIG. 6). In contrast, wild type animals that were treated with 4D5 showed little tumor growth over six weeks, with the maximum tumor size of around 200 mm³ (FIG. 6). However, $\gamma^{-/-}$ mice that were treated with 4D5 still exhibited substantial tumor growth over six weeks, with maximum tumor size of about 800 mm³. After six weeks, the animals were sacrificed and further quantitation of tumor size was achieved by weighing the tumors. These results confirm those obtained from measuring the tumor size in live mice (FIG. 7) indicating that the animals required expression of Fc receptors in order for the anti-tumor antibodies to mediate optimal anti-tumor activities.

A similar experiment was performed using mice of the same genotypes, but with a humanized version of 4D5 antibody (HERCEPTIN®) and the humanized version of an anti-CD20 antibody (RITUXAN®. HERCEPTIN® has been approved for the treatment of breast carcinoma and RITUXAN® has been approved for the treatment of B cell lymphoma. The results of these experiments are similar to those using 4D5 (FIGS. 8 and 9). These results indicate that the mechanism for eradicating human breast carcinoma growth in mice is dependent on the interaction of a tumor-specific antibody with Fc receptor-expressing cells. Furthermore, it should be noted that an antibody with human Fc, HERCEPTIN®, can interact with mouse Fc receptors in an animal containing a human tumor implant for testing the efficacy of humanized antibodies against human carcinomas.

The orthotypic athymic nude mouse tumor model was modified to generate a suitable model to address the role of Fc$\gamma$RII and Fc$\gamma$RIII in the anti-tumor response, in order to determine the contribution of interactions between the Fc domain and effector cell Fc$\gamma$Rs to the in vivo activity of HERCEPTIN® and RITUXAN®. The common $\gamma$ chain deficient mouse (FcRγ$^{-/-}$)(Takai et al., 1994, Cell 76:519), lacking the activation FcγRs, I and III or the FcγRIIB deficient mouse (Takai et al., 1996, Nature 379:346) were each mated with athymic nude mice to generate FcRγ$^{-/-}$/nu/nu and FcγRIIB$^{-/-}$/nu/nu mice for use in xenograft human tumor models. The anti-tumor activity of the anti-p185HER-2/neu antibody HERCEPTIN® (humanized IgG1)(Carter et al., 1992, PNAS USA 89:4285) and its mouse parent antibody 4D5 (mouse IgG1) in preventing the growth of the human breast carcinoma BT474M1, which over-expresses p185IHER-2/neu, was addressed in FcRγ$^{-/-}$ and +/+ athymic nude mice (FIGS. 10A–D). Tumor growth, measured as volume, was identical in homozygous γ$^{-/-}$ and +/+ nu/nu mice injected subcutaneously with 5×10$^6$ BT474M1 cells. In γ$^{+/+}$ mice, a single 4 μg/gm intravenous dose, followed by weekly 2 μg/gm i.v. injections resulted in near complete inhibition of tumor growth (tumor mass reductions of 90 and 96% in 4D5 and HERCEPTIN® treated mice) with only 4 of 17 mice developing palpable tumors. However, this protective effect of HERCEPTIN® and 4D5 was lost in γ$^{-/-}$ mice. Tumor mass in antibody treated γ$^{-/-}$ mice were reduced by just 29 and 44%, respectively and 14 of 15 mice developed palpable tumors. Similar results were obtained in the γ$^{-/-}$ nu/nu xenograft model on the mechanism by which the chimeric monoclonal IgG1 anti-CD20 antibody RITUXAN® inhibits B cell lymphoma growth in vivo. Tumor growth of the human B cell lymphoma cell line Raji is indistinguishable in γ$^{-/-}$ and +/+ nu/nu mice (FIGS. 10E–F). However, the protective effect of weekly i.v. doses of RITUXAN® (10 μg/gm) seen in γ$^{+/+}$ is eliminated in γ$^{-/-}$ nu/nu mice. RITUXAN® treatment of wild-type athymic mice resulted in reductions of tumor mass by more than 99% and no wild type mice developed palpable tumors. In contrast in γ$^{-/-}$ mice little protection was afforded by RITUXAN®; 6 of 7 mice developed palpable tumors and tumor mass reductions averaged just 23%.

In contrast, FcγRIIB$^{-/-}$ mice were dramatically more effective at arresting BT474 growth in this nude mouse model (FIG. 11). At a sub-therapeutic dose of antibody (0.4 μg/gm loading, 0.2 kg/gm weekly) tumor growth in RIIB deficient mice was completely arrested, demonstrating the involvement of the inhibitory RIIB pathway in this model as well. Of note, the gene dosage of RIIB is significant in mediating inhibitory responses. FcγRII$^{+/-}$ displayed an phenotype intermediate between RII$^{+/+}$ and RII$^{-/-}$ in the ability of HERCEPTIN® to modulate BT474M1 tumor growth. Nude mice are known to display elevated NK cell numbers, leading to the presumption that antibody protection in those mice are not representative of the protection seen in syngenic systems, as in human disease. The observation that RIIB deletion greatly enhances protection in nude mice indicates the involvement of effector cells other than NK cells, such as monocytes and macrophages in the protective response and further indicates that the FcR-dependent pathways are not restricted to an NK cell biased system but, as in the syngenic melanoma system, is likely to be relevant in other syngenic systems as well.

Although multiple mechanisms have been proposed for the ability of anti-tumor antibodies to mediate their effects in vivo, the data presented here suggest a dominant and necessary role for FcγR dependent binding for in vivo activity. This FcγR dependence appears to be a general requirement for effective anti-tumor activity in vivo since it has been observed for both syngenic and xenograft models for the three unrelated tumors and target antigens presented here. FcγR engagement involves both activation and inhibitory receptors and thus implicates monocytes and macrophages in the effector cell component of the protective response.

8. EXAMPLE: ANTIBODY ENGINEERED TO DISRUPT BINDING TO FcγR DISPLAYS REDUCED ANTI-TUMOR ACTIVITY

Figure 12C:
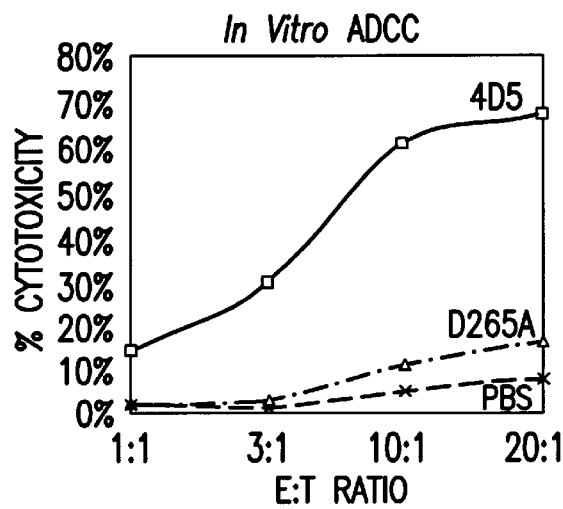
Figure 12D:
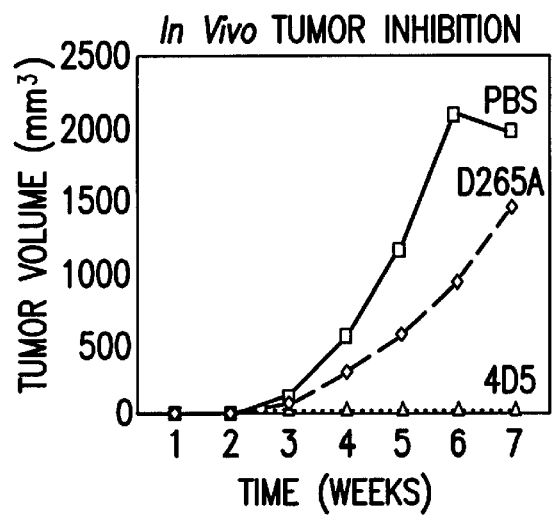

To further demonstrate the requirement of Fc-FcγR interactions in the protective response, a modification of the mouse IgG1 anti-HER2 antibody 4D5 was engineered to disrupt the ability of the antibody to engage cellular FcγR receptors while retaining its affinity for its cognate antigen p185 HER-2/neu. Based on alanine-scanning mutagenesis mapping of the murine IgG1 Fc domain binding for FcγR, a single amino acid replacement at residue 265 in the $C_H2$ domain of the mouse IgG1 heavy chain was found to dramatically reduce binding of IgG1-containing immune complexes to both FcγRII and III in a receptor coated plate assay (FIG. 12A). This residue is located at a site within the Fc portion of the IgG molecule thought to interact directly with surfaces of FcRs. The 265 (asp-4ala) mutation was placed in the 4D5 IgG1 heavy chain gene and transfected in parallel with the wild-type 4D5 IgG1 heavy chain into A293 cells along with the 4D5 kappa chain to produce 4D5 and mutant (D265A) antibodies. Since the mutation would not be expected to disrupt antibody-antigen interactions, as predicted, both 4D5 and D265A antibodies purified from transfected cell supernatants bound cellular p185HER-2/neu with equivalent avidity and had comparable in vitro growth inhibitory activity when added to BT474M1 expressing breast carcinoma cells in tissue culture (FIG. 12B). However while D265A retained the wild-type characteristics of in vivo half-life, antigenic targeting and functional p185HER-2/neu receptor blockade, the in vitro ADCC capacity of the mutant was lost as a consequence of its reduced affinity for FcγRIII on effector cells (FIG. 12C). In vivo the anti-tumor activity of D265A, when tested in the breast carcinoma BT474M1 xenograft model, displayed dramatically reduced anti-tumor activity as compared to 4D5 (FIG. 12D). Palpable tumors developed in all wild-type athymic mice treated with D265A while only in 2 of 5 mice treated with 4D5. D265A treatment reduced tumor volumes by 30% as compared to the 85% reduction seen with 4D5. The attenuated anti-tumor responses of D265A correlates with its impaired ability to activate FcR bearing effector cells despite its ability to inhibit tumor growth in vitro, supporting the conclusion that FcR engagement is a critical component of anti-tumor activity in vivo.

9. EXAMPLE: CONSTRUCTION OF AN IMMUNODEFICIENT MOUSE EXPRESSING HUMANIZED Fc RECEPTORS

In order to construct an animal which expressed human FcγRIII instead of mouse FcR in a nude background, BALB/cByJ-Hfh11$^{nu}$ immunodeficient mice were intercrossed to (C57BL/6x129)-[KO]FcγRIII-TgN(hFcγRIIIA) mice which were deficient in mouse FcγRIII but expressed human FcγRIIIA transgene. F1 animals were backcrossed to BALB/CByJ-Hfh11$^{nu}$. F2 animals were self-mated to generate the strain. These animals expressed human FcR in the same cells where human FcR is normally expressed (Li et al. J. Exp. Med. 183: 1259–1263 (1996)). Thus, human tumors may be implanted in these animals and a Fc-modified anti-tumor antibody can be tested for its ability to eradicate human tumor cells in vivo by interacting with human FcR-expressing effector cells.

The present invention is not to be limited in scope by the exemplified embodiments which are intended as illustrations of single aspects of the invention, and any clones, DNA or amino acid sequences which are functionally equivalent are within the scope of the invention. Indeed, various modifications of the invention in addition to those described herein will become apparent to those skilled in the art from the foregoing description and accompanying drawings. Such modifications are intended to fall within the scope of the appended claims. It is also to be understood that all base pair sizes given for nucleotides are approximate and are used for purposes of description.

All publications cited herein are incorporated by reference in their entirety.

What is claimed is:

1. A method for selecting an anti-tumor antibody comprising:
   (a) administering an antibody to a first non-human immunodeficient animal which is implanted with a human tumor;
   (b) administering said antibody to a second non-human immunodeficient animal which is implanted with said human tumor and said second animal is deficient in FcγRI, FcγRII, or FcγRIII; and
   (c) determining the ability of said antibody to retard tumor implant growth through an Fc gamma receptor pathway in the animal of step (a) as compared to the animal of step (b) wherein the ability of an antibody to retard tumor growth in step (a) is indicative of an anti-tumor antibody.

2. A method for selecting an anti-tumor antibody comprising:
   (a) administering an antibody to a first non-human immunodeficient animal which is implanted with a human tumor;
   (b) administering said antibody to a second non-human immunodeficient animal which is implanted with said human tumor and said second animal is deficient in FcγRI and FcγRIII; and
   (c) determining the ability of said antibody to retard tumor implant growth through an Fc gamma receptor pathway in the animal of step (a) as compared to the animal of step (b) wherein the ability of an antibody to retard tumor growth in step (a) is indicative of an anti-tumor antibody.

3. A method for selecting an anti-tumor antibody comprising:
   (a) administering an antibody to a first non-human immunodeficient animal which is implanted with a human tumor;
   (b) administering said antibody to a second non-human immunodeficient animal which is implanted with said human tumor and said second animal is deficient in FcγRI, FcγRII and FcγRIII; and
   (c) determining the ability of said antibody to retard tumor implant growth through an Fc gamma receptor pathway in the animal of step (a) as compared to the animal of step (b) wherein the ability of an antibody to retard tumor growth in step (a) is indicative of an anti-tumor antibody.

4. The method of claim 1, 2, or 3 in which the second animal expresses a human Fc gamma receptor.

5. The method of claim 1, 2, or 3 in which the first and second animals are mice.

6. The method of claim 1, 2, or 3 in which the antibody is a murine antibody.

7. The method of claim 1, 2, or 3 in which the antibody is a chimeric antibody.

8. The method of claim 7 in which the antibody is a humanized antibody.

9. The method of claim 1, 2, or 3 wherein the antibody is engineered to disrupt the ability to bind one or more of FcγRI, FcγRIIA, FcγRIIB, FcγRIIC, or FcγRIII.

10. The method of claim 1, 2, or 3 in which the first animal is a nude mouse.

11. The method of claim 1, 2, or 3 in which the first animal is a scid mouse.

12. The method of claim 1, 2, or 3 in which the first animal is a rag mouse.

13. The method of claim 1, 2, or 3 in which the human tumor is implanted in the animals prior to antibody administration.

14. The method of claim 1, 2, or 3 in which the human tumor is implanted in the animals after antibody administration.

15. The method of claim 1, 2, or 3 in which the human tumor is implanted in the animals simultaneous with antibody administration.

16. The method of claim 1, 2, or 3 wherein the antibody is engineered to enhance the ability of the antibody to bind one or more of FcγRI, FcγRIIA, FcγRIIB, FcγRIIC, or FcγRIII.

* * * * *